United States Patent [19]

Sherwin

[11] Patent Number: 4,458,094
[45] Date of Patent: Jul. 3, 1984

[54] PROCESS FOR FORMING NITROPARAFFIN
[75] Inventor: Martin B. Sherwin, Potomac, Md.
[73] Assignee: W. R. Grace & Co., New York, N.Y.
[21] Appl. No.: 341,679
[22] Filed: Jan. 22, 1982
[51] Int. Cl.³ .......................................... C07C 76/02
[52] U.S. Cl. .................................... 568/947; 568/948
[58] Field of Search .............................. 568/947, 948
[56] References Cited
U.S. PATENT DOCUMENTS
3,780,115 12/1973 Lhonore et al. ............... 568/948 X
4,260,838 4/1981 Lhonore et al. ................... 568/947
4,313,010 1/1982 Lhonore et al. ............... 568/947 X Primary Examiner—Leland A. Sebastian
Attorney, Agent, or Firm—Howard J. Troffkin

[57] ABSTRACT

An improved process for forming nitroparaffins by gaseous phase nitration of hydrocarbons higher than methane. The improvement comprises carrying out the nitration in the presence of a small amount of oxygenated hydrocarbons selected from aldehydes, ketones, alcohols, ethers and mixtures thereof.

10 Claims, 1 Drawing Figure

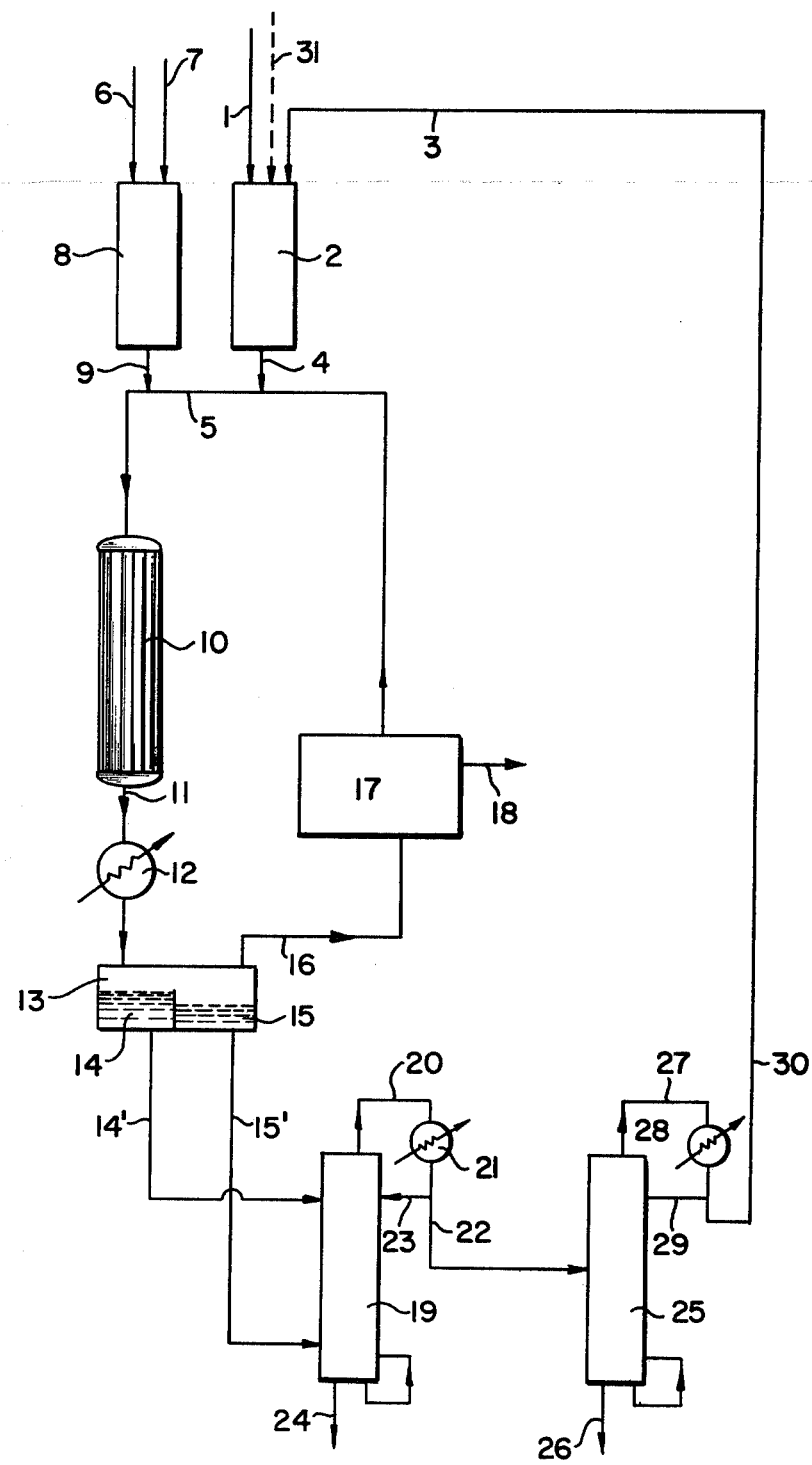

PROCESS FOR FORMING NITROPARAFFIN

BACKGROUND OF THE INVENTION

The present invention is directed to a process of producing nitroparaffins by gaseous phase nitration of a hydrocarbon feed stock containing a small amount of oxygenated hydrocarbon compounds. The present process gives higher yields of nitroparaffins and a significantly higher percentage of the nitroparaffin in the form of nitromethane.

Processes to form nitroparaffins by gaseous phase nitration are known. U.S. Pat. Nos. 3,780,115 and 3,869,253 teach that nitration of saturated hydrocarbons higher than methane can be accomplished by contacting the hydrocarbon feed with nitrogen peroxide in the presence of oxygen, such as in the form of air, under elevated temperature and pressure conditions. The reactant gases are preheated and then introduced into the reaction zone where the gaseous phase nitration is carried out at elevated pressure and at elevated temperature. The gaseous effluent emitted from the nitration reaction zone is rapidly quenched. The quenched mixture then enters a separator where the gaseous materials are removed for subsequent purification and recycling and the remaining organic and aqueous phase liquid materials are separated by decantation and the nitroparaffins are recovered by distillation. This nitration process yields a mixture of products having a predominance of nitropropanes.

French Publication No. 78/32,118 discloses that the nitroparaffins product mixture can be made to have an increased yield of nitromethane, the most commercially desired product, by utilizing ethane as the hydrocarbon feed in the homogeneous gas phase nitration. The nitration process can be further enhanced by recycling into the hydrocarbon feed some of the nitropropane product and/or by conducting the nitration in the presence of an inert gas such as nitrogen, hydrogen or argon.

U.S. Pat. No. 4,260,838, similar to the above French reference, teaches that the gas phase nitration process of U.S. Pat. Nos. 3,780,115 and 3,869,253 can be improved by altering the feed stock to obtain suitable percentages of different nitroparaffins as suits the needs of the marketplace. This patent teaches that the feed stock be made up of a mixture containing propane, preferably recycled nitroparaffin and possibly inert gas and/or another alkane. The nitrating agent can be either nitrogen peroxide or nitric acid.

Each of the conventional processes, such as those described in the above referenced patents, provides a nitroparaffin product mixture which is low in yield of nitroparaffin and/or low in yield of the most commercially desired compound, nitromethane.

SUMMARY OF THE INVENTION

A process for forming nitroparaffins in improved yield and in increased distribution of nitromethane therein by nitration of a hydrocarbon feed under elevated temperature and pressure suitable to conduct the nitration in a homogeneous gas phase. The process feed material comprises saturated hydrocarbon higher than methane, nitrogen peroxide, oxygen (such as in the form of air) and a small amount of oxygenated hydrocarbon.

DETAILED DESCRIPTION OF THE INVENTION

An improved process for the nitration of saturated hydrocarbons has been uncovered which requires the presence of small amounts of oxygenated hydrocarbons in the nitration reaction zone. The oxygenated hydrocarbons can be by-product oxygenated hydrocarbons (normally considered a waste material) conventionally stripped from the organic liquid phase during the recovery of the nitroparaffins and incinerated. Alternately, the oxygenated hydrocarbons can be obtained from sources external to the subject process, such as commercial materials.

The presently disclosed process is an improvement to presently known processes for homogeneous gaseous phase nitrations conducted under elevated temperature and pressure such as disclosed in U.S. Pat. Nos. 3,780,115; 3,869,253 and 4,260,838, which teachings are incorporated herein by reference.

Known processes generally perform homogeneous nitration by initially preheating the reactants before they are carried into the reaction zone. The preheating conditions are preferably substantially the same temperature and pressure as the reaction conditions.

The reactants are a saturated hydrocarbon compound or mixture of said compounds. The hydrocarbon should be a $C_2$ or greater hydrocarbon, preferably a $C_2$ to $C_5$ hydrocarbon with ethane or propane or mixtures thereof being most preferred. A part of the hydrocarbon feed can be recycled unreacted hydrocarbons which have been separated, purified and recondensed by conventional methods from the reaction product.

Nitrogen peroxide, usually supplied by conventional feed, such as, $NO_2$, $N_2O_4$, $HNO_3$, or mixtures thereof, and oxygen, usually in the form of air, can be separately preheated or, preferably are mixed together and then preheated. Similarly to the hydrocarbon feed, the nitrogen peroxide/oxygen feed stock can be partially obtained from recycled unreacted materials which have been separated and purified by conventional methods from the reaction products.

The feed may further contain inert gas such as nitrogen, carbon monoxide, hydrogen, carbon dioxide, argon or mixtures thereof. Further, the feed may contain amounts of up to about fifteen mole percent of less desired nitroparaffin compounds, such as 2-nitropropane, per hundred moles of $NO_2$ in the feed.

It has been presently unexpectedly found that the presence of small amounts of oxygenated hydrocarbons in the nitration reaction zone causes an increase in the yield of nitroparaffin products and an increase in the distribution of nitromethane, the most commercially desired compound of the nitroparaffins. The term "oxygenated hydrocarbon" as used in the present disclosure and claims appended hereto refers to compounds having at least one oxygen atom covalently bonded to a carbon atom, having from two to five carbon atoms and which are of the class of compounds of alcohols, aldehydes, ketones and ethers. The most preferred oxygenated hydrocarbon compounds are compounds having a structure such that at least one carbon atom within the compound which is covalently bonded (single or double bond) to an oxygen atom is also bonded to a methyl group, such as, for example, acetaldehyde, acetone, methyl ethyl ketone, ethanol, isopropanol, 2-butanol, diethyl ether, methylethyl ether and the like.

More specifically, the oxygenated hydrocarbon can be selected from alcohols such as $C_2$ to $C_5$ alkyl alcohols as, for example, ethanol, 1-propanol, 2-propanol, isopropanol, 2-butanol, tert-butanol and the like; aldehydes such as $C_2$ to $C_5$ aldehydes as, for example, acetaldehyde, propionaldehyde and the like; ketones such as $C_3$ to $C_5$ ketones as, for example, acetone, methylethyl ketone and diethyl ketone; and ethers such as $C_2$ to $C_5$ ethers as, for example, dimethylether, methylethyl ether, diethyl ether, methyl butyl ether and the like.

It is preferred that the oxygenated hydrocarbon feed be formed of lower i.e. $C_2$–$C_4$ compounds or mixtures of said compounds and preferably $C_2$ compounds, such as a mixture of acetaldehyde, acetone, ethanol or diethyl ether. The ratio of components will be dictated primarily by economics and availability.

The oxygenated hydrocarbon compounds preferably do not contain non-hydrocarbon groups except for the oxygen, as described above. However, the compounds may contain non-hydrocarbon groups which will not inhibit the subject process, such as nitriles, halides and the like. The supply of oxygenated hydrocarbons may also contain small amounts of other compounds, such as lower or higher homologs of the oxygenated hydrocarbons described above without interferring with the presently obtained unexpected result.

The oxygenated hydrocarbon feed can be obtained by recycling at least a portion of the oxygenated hydrocarbon by-product stream obtained as the overhead product from the oxygenate removal column in conventional systems. The overhead stream of the oxygenates removal column is generally composed of a major amount (about 40–80 weight percent) of a mixture of acetaldehyde and acetone in ratios of from about 1.5:1 to about 3:1 with the remainder of the stream containing methanol, ethanol, formaldehyde as well as other materials in varying quantities.

Alternately, the oxygenated hydrocarbon feed can be one or more of the above described compounds obtained from a source external from the present system, such as commercially obtained.

The oxygenated hydrocarbon feed can be preheated under temperature and pressure conditions substantially the same as described above for each of the other feed streams or, alternatively, can be combined with the hydrocarbon feed prior to preheating.

The condition and parameter ranges for conducting the homogeneous gaseous nitration of hydrocarbons are as follows. The feed materials are of ratios such that the atoms of carbon contained in the saturated hydrocarbon feed e.g. ethane or propane or mixtures thereof to moles of nitrogen peroxide are between about 8 and 12. The molar ratio of $O_2$ to $NO_2$ is from about 0.05 to 0.3. The reaction is carried out at elevated temperatures such that the process fluids in the reactor are of a temperature of from about 280° C. to 520° C. and at elevated pressure of from about 5 to 30 bars with from 8 to 14 bars being preferred. The inert gases in the feed (e.g. $H_2$, A, CO, $CO_2$, $N_2$) can be from about 0 to 30 volumes percent. The reaction contact time of the reaction gases within the reaction zone can be from about 1 to 20 seconds with the order of from 4 to 12 seconds being preferred.

Referring to the drawing to illustrate the subject process, hydrocarbon feed such as of ethane, propane or a mixture thereof is transported from a reservoir (not shown) by pipeline 1 to preheater 2. Preheater 2 is also used to preheat the oxygenated hydrocarbon being circulated through pipeline 3. The preheater is maintained at substantially the reaction zone entry temperature of 330° C. and pressure of about 10 bars. The preheated hydrocarbon/oxygenated hydrocarbon mixture is then passed through pipeline 4 to reactor intake pipeline 5. The nitrogen peroxide and the oxygen (as air) are introduced to preheater 8 via pipelines 6 and 7, respectively. The preheater 8 is maintained at temperature and pressure conditions substantially the same as that of preheater 2. The mixed preheated $NO_2/O_2$ gases pass through pipeline 9 to reactor intake pipeline 5 using gas-gas mixing devices such as spargers, venturis, etc. The preheated gases are passed through reactor 10 which may be in the form of a tubular reactor heated by salt at a temperature of approximately 330° C. and at a pressure of approximately 10 bars. Hot spot within the reactor can be from 420° C. to 520° C. The reactor effluents withdrawn through pipeline 11 are cooled to 20° C. in cooler 12 which uses super-cooled water to rapidly cool the gases. The cooled reactor effluents are separated in the separator 13. The liquid effluent separates into organic liquid phase 14 and aqueous liquid phase 15.

The uncondensed gaseous reaction effluents are removed from the separator 13 through pipeline 16. The uncondensed gaseous reaction effluents are a mixture of components composed predominantely of unreacted hydrocarbon feed (e.g. ethane, propane), nitric oxide and inert gases. These gaseous reaction effluents are then treated at station 17 in one of a variety of conventional manners before recycling back through reactor intake pipeline 5 as part of the feed to reactor 10. The specific modes of treatments chosen do not effect the present invention. For illustrative purposes, the gaseous effluent can be treated (a) by directly injecting oxygen into the gaseous effluent to re-oxidize the nitrogen oxide to nitrogen peroxide; (b) by cryogenically removing any hydrocarbon gases contained in the gaseous effluent prior to oxidizing the nitrogen oxide; or (c) by removing the nitric oxide from the gaseous effluent by absorption in ferrous sulfate solution and subsequent stripping followed by re-oxidizing the nitric oxide to peroxide. To prevent build-up of inert gases due to the recycling of treated gaseous effluent, a purge stream 18 is maintained.

The condensed organic and aqueous liquid phases 14 and 15, respectively, are removed from separator 13 and sent by pipelines 14' and 15' to an azeotropic column 19 which operates at a pressure of 1.25 bars or less and at temperatures of from 80° C. to 105° C. The mixture of nitroparaffins as well as other compounds having a boiling point lower than the nitroparaffins including the reaction zone by-product oxygenated hydrocarbons of alcohols, aldehydes ketones and ethers are azeotropically distilled overhead with their associative water and passed via pipeline 20, condenser 21 and pipeline 22 to an oxygenate removal column 25. Some of the distillate may be recycled to the azeotropic column 19 by pipeline 23. The majority of the water and the heavy by-products such as acids and the like are removed as bottom waste products through pipeline 24.

The oxygenate removal column 25 operates at a pressure of 1.25 bars or less and at a temperature range of from 30° C. to 95° C. The bottom product of column 25 is removed by pipeline 26 and is composed of a mixture of a major amount of nitroparaffin products, a lesser amount of water (from the prior azeotropic distillation) and may contain trace amounts of oxygenated hydrocarbon by-products. The material removed by pipeline 26 is subsequently chemically treated (not shown) to remove the trace oxygenated contaminants then fed to a dehydration column (not shown) and finally to a fractionation column (not shown) to recover pure nitroparaffin products.

The overhead effluent of column 25 is removed by pipeline 27 through condenser 28. The overhead effluent is normally very small in comparison to the bottom product and is made up of a mixture of light oxygenated hydrocarbon compounds of alcohols, aldehydes, ketones and ethers. Generally, the majority of the overhead effluent is made up of a mixture of acetaldehyde and acetone of about 40 to 80 percent in a weight ratio of from about 1.5:1 to 3:1. Due to small quantity of this effluent, its mixed composition and the difficulty of purification into its individual components, the effluent of column 25 has been considered in the past as having little value and normally incinerated.

It has been unexpectedly found that by utilizing the effluent material of the oxygenate removal column 25 as part of the feed to the nitration reactor 10 one obtains higher yields of nitroparaffin product and a greater percentage of the nitroparaffin product in the form of the most highly desired compound, nitromethane. The amount of oxygenated hydrocarbon to be present in the reactor 10 feed is up to about 10 weight percent of the hydrocarbon feed (fresh feed plus recycle) with from 1 to 5 weight percent being preferred. Oxygenated effluent from the oxygenated removal column 25 is normally approximately 20.0 weight percent of the fresh hydrocarbon feed entering pipeline 1. Alternately, or as part of start-up procedure, oxygenated hydrocarbons, as described above, singly or as a mixture, e.g. 3:1 to 1:3 acetaldehyde/acetone, can be introduced in amounts described above for recycled material into the feed by pipeline 31. In either case the presence of small quantities of oxygenated hydrocarbons in the total feed causes a significant shift of the distribution of the nitroparaffin compounds to give generally from 10 to 25 percent greater yields of nitromethane.

In one example, a feed mixture composed of 33 volume percent ethane; 23 volume percent propane; 13 volume percent $NO_2$; 3.5 volume percent $O_2$ and the remainder inert gases was reacted in a tubular reactor at operating pressure of 10 bars absolute, a salt temperature of 330° C. and a contact time of 8 seconds. The conversion of the hydrocarbons, ethane and propane, was 6 and 12 percent, respectively. The carbon yield distribution of the products were 12.8 percent nitromethane; 14.0 percent nitroethane; 20 percent combined nitropropanes; 30.3 percent inerts ($CO,CO_2$) and 22.8 percent oxygenated hydrocarbons. The nitroparaffin distribution by weight was 41 percent nitromethane; 27.7 percent nitroethane and 31.3 percent combined nitropropanes.

In comparison, when 1.5 weight percent of the mixed oxygenated hydrocarbons collected as overhead effluent in the nitration separation were recycled to the above reactor the overall nitroparaffin production increased by 7.4 percent and the nitromethane production increased by 18 percent by weight.

In another production comparison, five homogeneous gaseous nitration reaction runs were conducted with recycling of 13 volume percent of nitropropanes relative to the $NO_2$ feed. The feed consisted of 34.6 volume percent propane, 22.4 volume percent ethane, 1.8 volume percent nitropropane, 3.8 volume percent $O_2$, 13.1 volume percent $NO_2$ and 24.3 volume percent $N_2$. The reactor had a hot spot temperature of 475° C. with a salt bath temperature of 318° C. and pressure of 10 bars. The materials were cooled, separated, azeotropic distilled and separated from the oxygenated material. The average production for each nitroparaffin was (in parts/hour): 408 parts nitromethane; 287 parts nitroethane; 153 parts 1-nitropropane; and 79 parts 2-nitropropane. Total nitroparaffin 927 parts.

In comparison the above runs were repeated except that a 2.3:1 weight mixture of acetaldehyde/acetone was introduced as part of the hydrocarbon feed at levels of 2.16 moles per 100 moles of ethane and propane. The average production for each nitroparaffin was (in parts/hour): 479 parts nitromethane; 270 parts nitroethane; 127 parts 1-nitropropane and 64 parts 2-nitropropane. Total nitroparaffin 940 parts.

It is clear that the presence of small amounts of oxygenated compounds in the reaction zone increases the yield of nitroparaffins and the distribution to nitromethane.

While the invention has been described in connection with certain preferred embodiments, it is not intended to limit the invention to the particular form set forth, but, on the contrary, it is intended to cover such alternatives, modifications and equivalents as defined by the appended claims.

What is claimed:

1. In a homogeneous gaseous phase nitration process for the formation of nitroparaffins by contacting in a reaction zone a hydrocarbon or mixture of hydrocarbons higher than methane, nitrogen peroxide and oxygen at elevated temperatures and at elevated pressures; cooling the reaction zone effluent; separating the resulting liquid phase effluent from the non-condensed gaseous effluent; separating the organic nitroparaffin containing phase from the liquid phase effluent; and recovering the nitroparaffin components; the improvement comprising contacting said hydrocarbon, nitrogen peroxide and oxygen reactants in said reaction zone in the presence of a small amount of $C_2$ to $C_5$ oxygenated hydrocarbon feed selected from alcohols, aldehydes, ketones, ethers and mixtures thereof.

2. The process of claim 1 wherein the oxygenated hydrocarbons present in the reaction zone are oxygenated hydrocarbons obtained during the separation and recovery of the organic nitroparaffins contained in the liquid phase reaction zone effluent.

3. The process of claim 1 wherein the oxygenated hydrocarbons present in the reaction zone are oxygenated hydrocarbons at least partially obtained from a source external to said process.

4. The process according to claim 2 wherein the hydrocarbon is selected from propane, ethane or mixtures thereof.

5. The process according to claim 3 wherein the hydrocarbon is selected from propane, ethane or mixtures thereof.

6. The process according to claim 2, 3, 4 or 5 wherein said $C_2$ to $C_5$ oxygenated hydrocarbon is present in a small amount of up to 10 percent by weight based on the hydrocarbon present in the reaction zone.

7. The process according to claim 6 wherein said oxygenated hydrocarbon compound, or mixtures of said compounds, is a compound having at least one oxygen atom and at least one methyl group bonded to a common carbon atom.

8. The process according to claim 2 or 3 wherein the reaction zone feed mixture further contains up to 15 mole percent of at least one nitroparaffin compound per 100 moles of nitrogen dioxide.

9. The process according to claim 2, 3, 4 or 5 wherein the reaction zone is maintained at a reaction pressure of between 7 and 30 bars; a reaction fluid temperature of between 280° and 520° C.; a ratio of hydrocarbon carbon atom to mole of nitrogen peroxide of from about 8 to 12; a mole ratio of $O_2$ to $NO_2$ of from about 0.05 to 0.3.

10. The process according to claim 4 wherein a majority of said oxygenated hydrocarbons is a mixture of acetaldehyde and acetone in a weight ratio of about 1.5:1 to 3:1.

* * * * *